United States Patent [19]

Boschelli et al.

[11] Patent Number: 5,462,952
[45] Date of Patent: Oct. 31, 1995

[54] FENAMATE 1,3,4-THIADIAZOLES AND 1,3,4-OXADIAZOLES AS ANTIINFLAMMATORY AGENTS

[75] Inventors: Diane H. Boschelli, Plymouth; David T. Connor; Milton L. Hoefle, both of Ann Arbor, all of Mich.

[73] Assignee: Warner-Lambert Company, Morris Plains, N.J.

[21] Appl. No.: 118,480

[22] Filed: Sep. 8, 1993

Related U.S. Application Data

[63] Continuation of Ser. No. 769,562, Oct. 2, 1991, abandoned, which is a continuation of Ser. No. 506,768, Apr. 12, 1990, abandoned, which is a continuation-in-part of Ser. No. 364,407, Jun. 9, 1989, abandoned.

[51] Int. Cl.$^6$ .................. C07D 271/113; A61K 31/41; A01N 43/82
[52] U.S. Cl. .................. 514/364; 548/136; 548/141; 548/143; 548/144
[58] Field of Search ................... 548/143, 144; 514/364

[56] References Cited

U.S. PATENT DOCUMENTS 3,294,813  12/1966  Juby.

FOREIGN PATENT DOCUMENTS 0084673  of 1983  European Pat. Off..
1930263   1/1971   Germany .................. 548/149
1166861   5/1969   United Kingdom.

OTHER PUBLICATIONS

Davidson, Monatsch Chem. 115, 565 (1971) Abstract.
Monatshefte fur Chemie, J. S. Davidson, vol. 115, No. 5, May 1984, pp. 565–571 1984.
Bulletin de la Societe Chemique de France, No. 5, 1985, pp. 859–864, L. Legrand et al.
EPO Search Report 90 110 900.9 * denotes previously uncited references which are now attached. 1991.
Derwent Abstract No. 1988–156224/23 Referring to European Application No. 269,981.
Derwent Alerting Bulletin J8–B, vol. 88, No. 21 by Kanegafuchi Kagaku Referring to Japanese Application 88024498 (1988).
Derwent Abstract No. 1988–180570/26 by Eisai KK, Referring to Japanese Application No. J63119–461.
Derwent Abstract No. (1988)–178798/26 by Eisai KK, Referring to Japanese Application No. J63115–859.
Derwent Abstract No. (1988)–147234/21 Referring to U.S. Pat. No. 4,743,606.
Derwent Abstract No. (1987)–140934/20 Referring to Japanese Application No. J62,081,343.
Derwent Abstract No. (1987)–051809/08 Referring to European Application No. 211670.
Derwent Abstract No. (1987)–203585/29 by Yamanouchi Pharm KK, Referring to Japanese Application No. 62132871.
MISC. Derwent Abstract No. (1988)–178974/26 Referring to Japanese Application No. J63115–860–A.
MISC. Derwent Abstract No. (1987)–216873/31 Referring to Japanese Application No. J62142–162–A.
MISC. Derwent Abstract No. (1982)–74952E/36 Referring to U.S. Pat. No. 4,636,516.

*Primary Examiner*—Robert Gerstl
*Attorney, Agent, or Firm*—Ronald A. Daignault; Charles W. Ashbrook

[57] ABSTRACT

The present invention is novel compounds which are 1,3,4-thiadiazoles and 1,3,4-oxadiazoles, and pharamaceutically acceptable acid addition or base salts thereof having activity as inhibitors of singly or together 5-lipoxygenase and cyclooxygenase, and pharmaceutical compositions or methods of use therefor.

31 Claims, No Drawings

FENAMATE 1,3,4-THIADIAZOLES AND 1,3,4-OXADIAZOLES AS ANTIINFLAMMATORY AGENTS

This application is a continuation of Ser. No. 07/769,562, filed Oct. 2, 1992, now abandoned, which is a continuation of application Ser. No. 07/506,768, filed Apr. 12, 1990, abandoned, which is a continuation-in-part of application Ser. No. 07/364,407, filed Jun. 9, 1989, now abandoned.

BACKGROUND OF THE INVENTION

The present invention is novel compounds which are 1,3,4-thiadiazoles and 1,3,4-oxadiazoles, and pharmaceutically acceptable acid addition or base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, fever, and the like. Thus, the present invention is also a pharmaceutical composition or method of use therefor.

Although fenamates are known among antiinflammatory agents and various thiadiazoles and oxadiazoles are known as useful substituents in derivations thereof, for example, together with 3,5-di-tertiary-butyl-4-hydroxyphenyl groups as disclosed in copending application PD-3815, the present combination of ring systems, substituents and moieties is not among those previously known. Other compounds having ring systems also include various thiadiazoles and oxadiazoles and references discussing such compounds are disclosed in PD-3815 and it is therefore incorporated by reference here. Among these disclosures are use for treating inflammation as is found here but the differences between the known compounds and the present compounds are readily apparent with no teaching to make obvious such differences would also be useful for treatment of the conditions taught here.

SUMMARY OF THE INVENTION

The present invention is a compound of the formula (I)

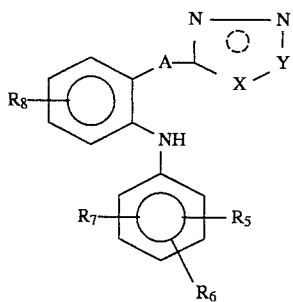

and pharmaceutically acceptable salts thereof, wherein

A is a bond, $CH_2$ or $CH=CH$;

X is oxygen or sulfur;

Y is (1) C—$SR_1$ wherein $R_1$ is independently hydrogen or lower alkyl

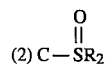

wherein $R_2$ is lower alkyl

wherein $R_2$ is as defined above, (4) C—$NR_1R_3$ wherein $R_1$ is independently as defined above and $R_3$ is hydrogen or lower alkyl, (5) $COR_1$ wherein $R_1$ is independently as defined above, (6) $CR_4$ wherein $R_4$ is lower alkyl, halogen, $CF_3$, $CO_2R_1$, or

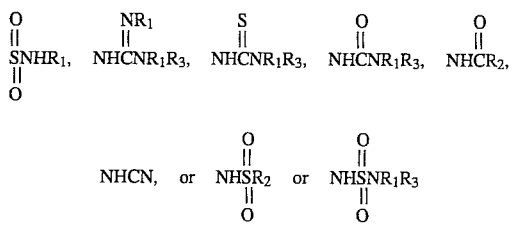

wherein $R_1$, $R_2$, and $R_3$ are independently as defined above;

$R_5$, $R_6$, $R_7$, and $R_8$ are independently hydrogen, fluoro, chloro, bromo, iodo, trifluoromethyl, lower alkyl, CN, hydroxy, lower alkoxy, —$S(O)_n$-lower alkyl, $NO_2$, or $NR_9R_{10}$ wherein $R_9$ or $R_{10}$ are independently H, lower alkyl or acyl; and n is an integer of 0 through 2.

The present invention is also a pharmaceutical composition for the treatment of conditions advantageously affected by the inhibition of 5-lipoxygenase, cyclooxygenase or both which comprises an amount effective for the treatment of the condition of a compound of the formula I and the pharmaceutically acceptable acid addition or base salt thereof together with a pharmaceutically acceptable carrier. The condition is meant to include, for example, arthritis including rheumatoid arthritis, osteoarthritis; or other inflammatory conditions or diseases such as inflammatory bowel disease, gastrointestinal ulcers; allergic diseases; asthma; pain; fever; cardiovascular conditions including ischemic heart disease and atherosclerosis; ischemia-induced cell damage, particularly brain damage caused by stroke; and psoriasis; but preferably inflammatory diseases.

The present invention is also a method for treatment of the condition as noted above in a meal, including humans, suffering therefrom with a compound of the formula I or the pharmaceutically acceptable acid addition or base salt thereof, in unit dosage form. The invention also provides for use of any such compound of formula I or salt thereof in the manufacture of a medical therapeutic agent.

Pharmaceutical composition or use of the compound or salt of formula I is meant to include treatment understood to be prophylactic pertinent to the foregoing named condition.

DETAILED DESCRIPTION OF THE INVENTION

In the compounds of formula (I) the term "lower alkyl" includes an alkyl group of from one to six carbons such as methyl, ethyl, propyl, butyl, and the like and isomers thereof. Halogen is chloro, bromo or fluoro. Acyl is of from $C_2$ to $C_4$ carbon atoms, such as acetyl, propionyl, butyryl, and isomers thereof.

The compounds I of the invention may exist as tautomers, for example, when Y is $CSR_1$, $COR_1$ or $CNR_1R_2$ and $R_1$ is hydrogen. These compounds are readily determined from art recognized tautomerism. Such tautomers are, for example, represented by formula I' and I" as follows:

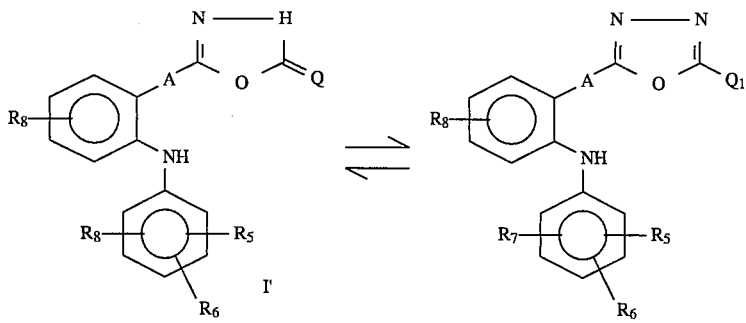

or

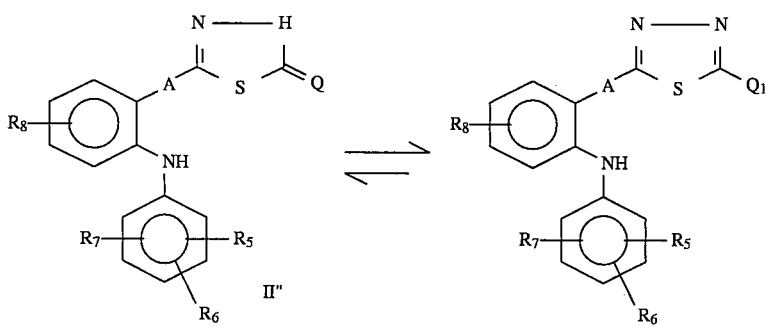

wherein Q is O, NH, or S and $Q_1$ is OH, $NH_2$ or SH respectively.

Appropriate compounds of formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; choline; guanidine; N-methylglucosamine; N-methylglucamine; L-glutamine; N-methylpiperazine; morpholine; ethylenediamine; N-benzylphenethylamine; tris(hydroxymethyl) aminomethane; and the like. (See for example, "Pharmaceutical Salts," *J. Pharm. Sci.*, 66(1):1–19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or pharmacologically acceptable salt thereof to achieve a therapeutic effect will, of course, vary both with the particular compound, the route of administration, the mammal under treatment, and the particular disorder or disease concerned. A suitable dose of a compound of formula I or pharmacologically acceptable salt thereof for a mammal suffering from, or likely to suffer from any condition as described hereinbefore is 0.1 µg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng–100 µg of the compound per kilogram, typically about 0.1 µg/kg.

In the case of oral dosing for the treatment or prophylaxis of arthritis or inflammation in general, due to any course, a suitable dose of a compound of formula I or pharmacologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula (I) or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more excipients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended in PBS containing 1.0 mM calcium at a density of $2 \times 10^6$ cells/ml. Cells are incubated with and without test agent (in DMSO) (1% DMSO is without effect on arachidonic acid metabolism) for ten minutes at room temperature. Calcium ionophore A23187 (5 µM) is added and cells are incubated for seven minutes at 37° C. The reaction is stopped by chilling the tubes on ice for ten minutes. Cells are separated by centrifugation and the supernatant is stored at −20°. Aliquots (100 µl) are analyzed for $LTB_4$ and $PGF_{2\alpha}$ using radioimmunoassay kits as provided by the supplier.

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield, N.J.) in 10 ml of sterile saline (0.9%) solution (Travenol). The solution is vortexed for 30 to 45 minutes. Animals are dosed with compound one hour before carrageenan challenge. Foot paw edema is induced by injecting 0.10 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured five hours after carrageenan. The difference between the 5-hour and the initial paw volume is expressed as delta edema. The delta edema for each test group of animals is used to calculate the percent inhibition of edema achieved by the compound at the test dose compared with the vehicle control group. The data in Table 1 (the dose at which swelling is inhibited by the noted) is calculated by probit analysis for the dose at which 40% inhibition occurs.

Tables 1 and 2 contain biochemical data obtained from the whole cell assay described above as $IC_{50}$s which are calculated as the concentration of test compound causing 50% inhibition of $LTB_4$ or $PGF_{2\alpha}$ formation. Table 2 also provides the dose at which 40% of swelling is inhibited in the CFE-2 assay.

TABLE 1

| Example | ARBL[a] | ARBC[b] |
|---------|---------|---------|
| 2 | 97 | 0.7[c] |
| 4 | .60[c] | 6.1[c] |
| 7 | 88 | N[d] |

[a] % inhibition of $LTB_4$ at 16 µM
[b] % inhibition of $PGF_{2\alpha}$ at 16 µM
[c] $IC_{50}$
[d] Less than 40% inhibition at 16 µM

TABLE 2

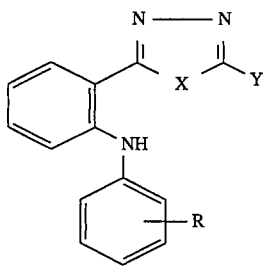

| R | X | Y | ARBL[1] | ARBC[1] | CFE[2] |
|---|---|---|---|---|---|
| 2,6-diCl, 3-Me | O | OH | N | N | |
| 2,6-diCl, 3-Me | O | SH | 0.74 | 0.70 | |
| 2,6-diCl, 3-Me | O | NH$_2$ | 45 @ 10 | N | |
| 2,6-diCl, 3-Me | O | H | N | N | |
| 2,6-diCl, 3-Me | O | SMe | N | 55 @ 10 | |
| 2,6-diCl, 3-Me | O | SO$_2$Me | 6.32 | 3.00 | |
| 2,6-diCl, 3-Me | O | SOMe | 0.91 | 1.79 | |
| 2,6-diCl, 3-Me | O | NHCNH$_2$ NH | 46 @ 10 | N | |
| 2,6-diCl, 3-Me | O | NHCN | .89 | .25 | |
| 2,3-diMe | O | OH | N | N | |
| 2,3-diMe | O | SH | 1.0 | 0.61 | |
| 3-CF$_3$ | O | SH | 0.77 | 0.27 | 8.5 |
| 3-CF$_3$ | O | NH$_2$ | 0.68 | 7.12 | |
| 3-CF$_3$ | O | SMe | N | 44 @ 10 | |
| 3-CF$_3$ | O | SO$_2$Me | N | 48 @ 10 | |
| 3-CF$_3$ | O | NHCN NH | 2.99 | 1.04 | |
| 3-CF$_3$ | O | NHCNH$_2$ | 100 @ 10 | N | |
| 2,6-diCl, 3-Me | S | SH | 100 @ 16 | 47 @ 16 | |
| 2,6-diCl, 3-Me | S | NH$_2$ | 0.6 | 6.1 | |
| 2,6-diCl, 3-Me | S | SMe | N | 60 @ 10 | |
| 2,6-diCl, 3-Me | S | SOMe | 3.3 | 8.48 | |
| 3-CF$_3$ | S | SH | 0.87 | 0.85 | 4.7 |
| 3-CF$_3$ | S | NH$_2$ | 0.69 | 11 | |
| 3-CF$_3$ | S | SMe | 66 @ 10 | 44 @ 10 | |
| 3-CF$_3$ | S | SOMe | 100 @ 10 | 51 @ 10 | |

[1]IC$_{50}$ (μM) or % inhibition at given concentration (μM).
[2]ID$_{40}$ (mg/kg).
N Not active at the screening dose.

Accordingly, the present invention also includes a pharmaceutical composition and a method for treating a condition selected from those listed above comprising administering to mammals, including humans, suffering therefrom either orally or parenterally the corresponding pharmaceutical composition. The composition comprises a compound of the formula I in appropriate unit dosage form.

In addition to the compounds of formula I, the pharmaceutical compositions may also contain other active ingredients, such as cyclooxygenase inhibitors, nonsteroidal antiinflammatory drugs (NSAIDS), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDS can be characterized into five groups:

(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^{30}$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefanamic acid, meclofenamic acid, flufenamic acid, (niflumic acid), and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

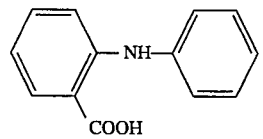

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

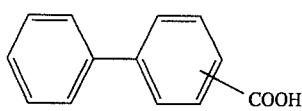

which can bear a variety of substituents and in which the free —COOH group can be in the form of a pharmaceutically acceptable salt group, e.g., —COO—Na$^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

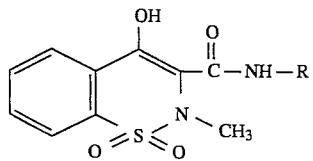

wherein R is an aryl or heteroaryl ring system.

The following NSAIDS may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDS which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compound of the formula I and their salts may be prepared generally by the following processes.

For the compound of the formula I wherein A is a bond and X is S when Y is $NH_2$ or a derivative thereof, or X is O when Y is S or O or the derivative thereof, the Scheme 1 provides a method of preparation as follows:

Scheme 1

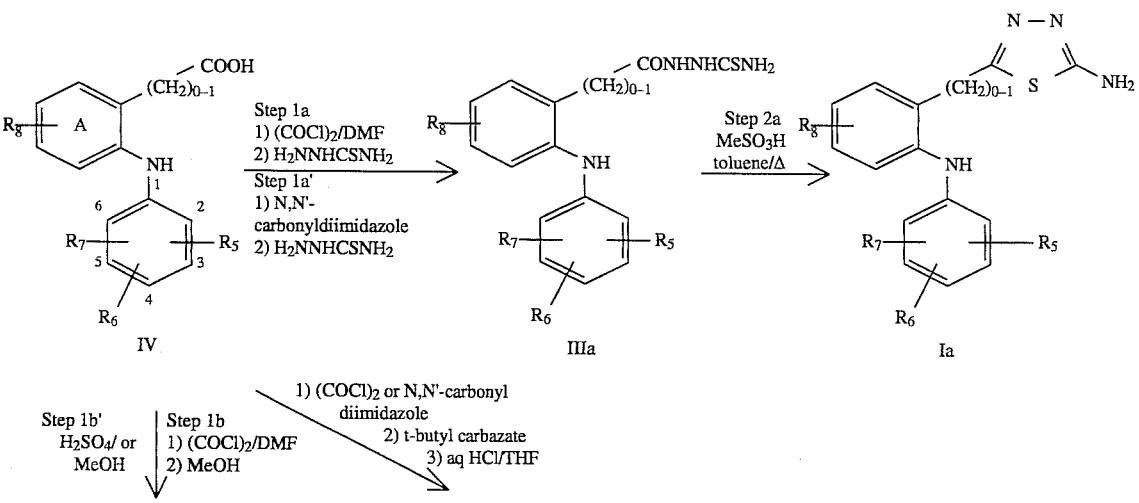

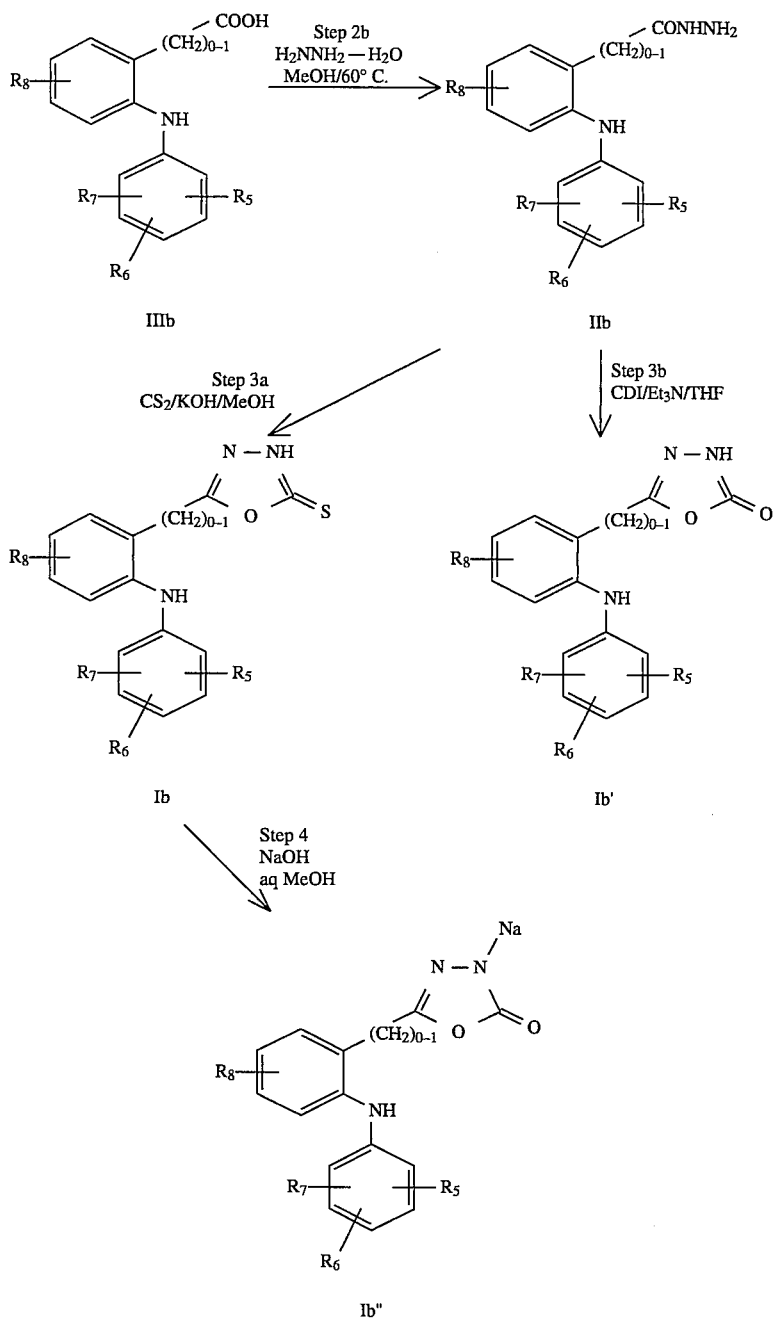

-continued
Scheme 1

Description of Scheme I

In Step 1a, a fenamate of the formula IV wherein $R_5$, $R_6$, $R_7$ and $R_8$ are as defined above but having one of $R_5$, $R_6$ and $R_7$ in each of the 2 and 6 positions of the "B" ring is treated with oxalyl chloride or thionyl chloride in tetrahydrofuran, chloroform, or preferably methylene chloride, that contains from one drop to one equivalent of dimethylformamide.

The resulting acid chloride is then treated with thiosemicarbazide in dioxane, tetrahydrofuran, methylene chloride or preferably pyridine to give the hydrazide thioamide of the formula IIIa wherein $R_5$, $R_6$, $R_7$ and $R_8$ are as defined for Step 1a.

Alternatively the acid of formula IV is treated with N,N'-carbonyldiimidazole to give an imidazolide. This intermediate is treated with thiosemicarbazide in refluxing pyridine to give the hydrazide thioamide of the formula IIIa.

In Step 2a, the product of Step 1a is heated at reflux in toluene with polyphosphoric acid or preferably methane sulfonic acid to give the amino thiadiazole of the formula Ia wherein $R_5$, $R_6$, $R_7$ and $R_8$ are as defined for Step 1a'.

In Step 1b, a fenamate of the formula IV again having one of $R_5$, $R_6$ and $R_7$ in each of positions 2 and 6 of the "B" ring is treated first with oxalyl chloride or thionyl chloride in tetrahydrofuran, chloroform or preferably methylene chloride that contains from one drop to one equivalent of dimethylformamide. The resulting acid chloride from 1) is added to an alcohol, such as methanol, ethanol and the like to give the corresponding ester of the formula IIIb wherein $R_5$, $R_6$, $R_7$ and $R_8$ are as defined for 1b.

Alternatively the acid is heated at reflux in an alcohol, preferably methanol, in the presence of sulfuric acid to give the ester.

Esters of fenamates are known compounds and further details on their preparation can be found in P. F. Juby et al, *J. Med. chem.*, 11, 111 (1968).

In Step 2b, the ester in methanol or ethanol is treated with an excess of hydrazine hydrate to give the hydrazide of the formula IIb wherein $R_5$, $R_6$, $R_7$ and $R_8$ are as defined above.

The hydrazide II or IIb can alternatively be prepared by treatment of the acid chloride or imidazolide with t-butyl carbazate in THF, then heating with aqueous hydrochloric acid and tetrahydrofuran.

In Step 3a, the hydrazide of the formula IIb and carbon disulfide in absolute methanol or ethanol is treated with base, preferably potassium hydroxide at 0° C., followed by heating at reflux to give the oxadiazole thione of the formula Ib wherein $R_5$, $R_6$, $R_7$ and $R_8$ are as defined above.

In Step 3b, N,N'-carbonyldiimidazole, phosgene or a phosgene equivalent is added to the hydrazide of the formula IIb in tetrahydrofuran containing 0 to 3 equivalents of an organic base, such as triethylamine to give the oxadiazolone of the formula Ib' wherein $R_5$, $R_6$, $R_7$ and $R_8$ is as defined above.

In step 4, the oxadiazole thione of the formula Ib is suspended in methanol or ethanol and treated with 1.0 equivalents of 1N aqueous sodium hydroxide to give the sodium salt of the oxadiazole thione of the formula Ib" wherein $R_5$, $R_6$, $R_7$ and $R_8$ is as defined above.

Conditions within the description of Scheme 1 above and variations in the description are known or can be readily determined from analogous reactions known to one of ordinary skill in the art.

For the compound of formula I wherein A is a bond and X is S and Y is S or derivatives thereof, the Scheme 2 provides a method of preparation as follows:

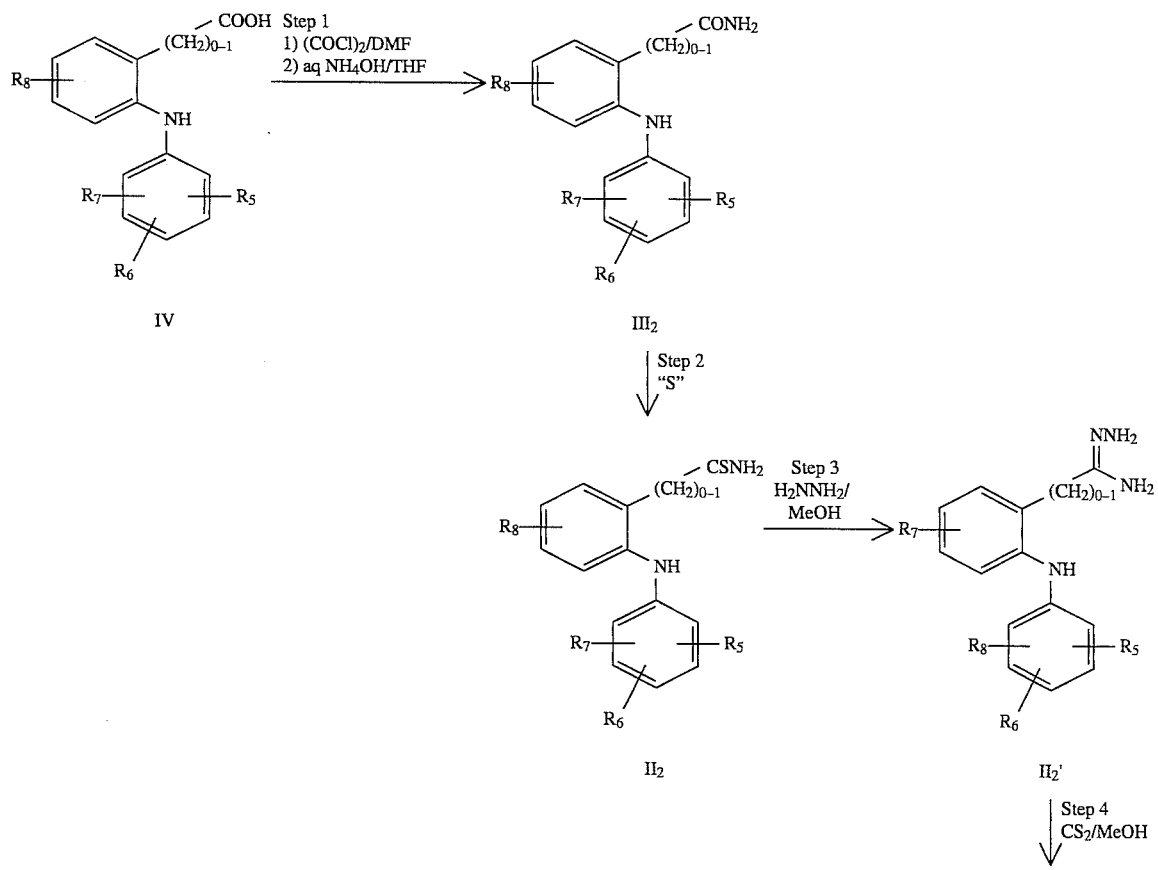

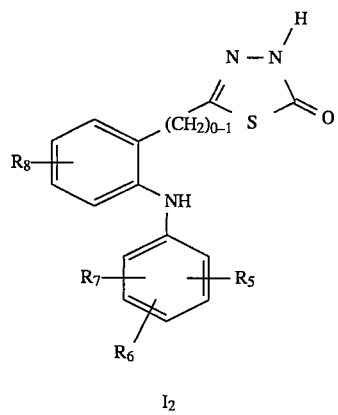

I₂

Description of Scheme 2

In Step 1, the aforesaid acid chloride prepared in 1) from a compound of the formula IV is added to a mixture of aqueous ammonium hydroxide in tetrahydrofuran in 2) to give the corresponding amide of the formula $III_2$ wherein $R_5$, $R_6$, $R_7$ and $R_8$ are as defined above.

Alternatively the amides of the formula $III_2$ can be obtained by treating the corresponding methyl or ethyl ester of the formula IIIb in Scheme I with ammonia.

Amides of fenamates are known compounds and analogous methods for the preparation of appropriate amides of the formula $III_2$ can be found in P. F. Juby, et al, *J. Med. Chem.*, 11, 111 (1968).

In Step 2, the amide of formula $III_2$ is dissolved in an ether solvent, preferably dioxane and treated with phosphorous pentasulfide to give the thioamide of the formula $II_2$ wherein $R_5$, $R_6$, $R_7$ and $R_8$ are as defined above. The amide $III_2$ can also be treated with Lawesson's reagent in an ether such as tetrahydrofuran to give the thioamide of the formula $II_2$.

In Step 3, the thioamide $II_2$ is treated with hydrazine in methanol or ethanol to give the amidrazone of the formula $II_2'$ wherein $R_5$, $R_6$, $R_7$ and $R_8$ are as defined above.

In Step 4, the amidrazone $II_2'$ in an alcohol, such as ethanol or methanol or in an ether solvent is treated with carbon disulfide to give the thiadiazole thione of the formula I2 wherein $R_5$, $R_6$, $R_7$ and $R_8$ are as defined above.

Again conditions within the description of Scheme 2 above and variations in the description are known or can be readily determined from analogous reactions known to one of ordinary skill in the art.

For the compound of formula I wherein A is a bond, $CH_2$ or HC=CH and X is O when Y is S or the derivatives thereof the Scheme 2a provides an alternative method or for further processes which are all variations of those shown in above Schemes 1 or 2 but where A is HC=CH, the Scheme 3, provides a method of preparation as follows:

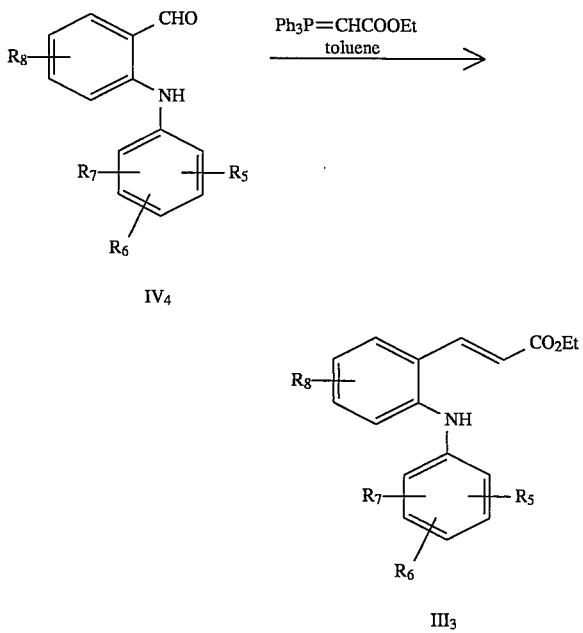

Scheme 3

IV₄

III₃

Description of Scheme 3

Where A of the invention is CH=CH, the intermediate-unsaturated ester of the formula $III_3$ wherein $R_5$, $R_6$, $R_7$ and $R_8$ are as defined above is obtained by treatment of an aldehyde of the formula $IV_4$ wherein $R_5$, $R_6$, $R_7$ and $R_8$ are as defined above with (carbethoxymethylene)triphenylphosphorane in toluene. Alternatively the phosphonate modification of the Wittig reaction could be utilized employing NaH, or a similar base. In either case the conditions of the treatment/modification are known or are analogous to those known to ordinarily skilled artisans.

Scheme 4 provides methods for the conversion of compounds of formula I wherein Y is C—SH to compounds of type I wherein Y is C—$SOR_2$, C—$SO_2R_2$, C—$OR_1$, $CNR_1R_3$, or C—NHCN. The conversion of Y is C—OH to Y is C—$OR_2$ is also shown in Scheme 4.

Scheme 4

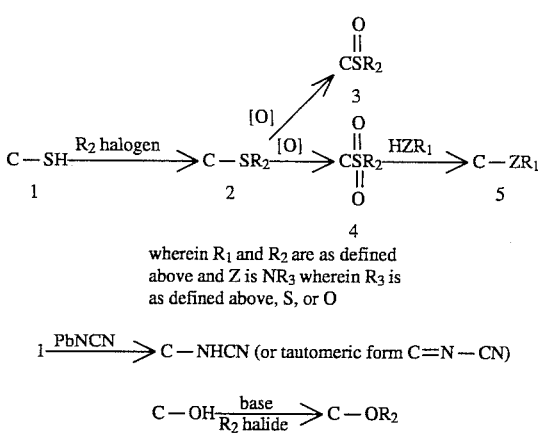

wherein $R_1$ and $R_2$ are as defined above and Z is $NR_3$ wherein $R_3$ is as defined above, S, or O $1 \xrightarrow{PbNCN} C—NHCN$ (or tautomeric form C=N—CN)

$C—OH \xrightarrow[R_2 \text{ halide}]{\text{base}} C—OR_2$ wherein $R_2$ is as defined above.

Scheme 4 indicates various standard transformations of Y.

Treatment of compounds of type 1, wherein Y is C—SH with bases such as KH, NaH, or t-BuOK in the presence of $R_2$halogen, where $R_2$=H or alkyl, using a protic solvent such as diethyl ether, tetrahydrofuran, or dimethylformamide, gives compounds of type 2. Treatment of 2 with an oxidizing agent such as $KMnO_4$, $H_2O_2$ in acetic acid or m-chloroperbenzoic acid (MCPBA) gives sulfones of type 4. Treatment of 4 with HZR' in the presence or absence of a base where Z is O, S, or $NR^3$ gives compound 5. Treatment of 2 with one equivalent of MCPBA, $H_2O_2$ or $NaIO_4$ gives 3.

When compounds where Y is C—OH are treated with alkylhalides ($R_2X$) in the presence of a base such as NaH, NaOH, KOH, KH, LiOH, t-BuOK, or triethylamine, then the resulting products are ethers.

Scheme 5 provides methods for the conversion of compounds of type 1 wherein Y is C—$NH_2$ to compounds of type 1 wherein Y is C—$OR_1$, C—$SR_1$, C—Halogen, C—$NHSO_2R_2$, C—$NHCONHR_1$, and C—$NHCSNHR_1$.

Scheme 5

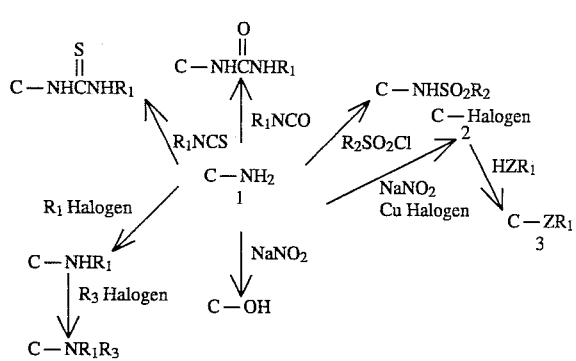

wherein $R_1$, $R_2$, and $R_3$ are as defined above.

The transformations shown in Scheme 5 are standard synthetic reactions. For example, 1 (Y=C—$NH_2$) is treated with $NaNO_2$, Cu halogen and H halogen (Sandmeyer reaction conditions) to give 2 (Y=C—Cl). Treatment of 2 with $HZR_1$ (Z is O, S or $R_3$) gives 3 (Y=C—$ZR_1$).

One of skill in the art would recognize any necessary sequence or variations in the sequence and would recognize variations in appropriate reaction conditions from analogous reactions which may be appropriately used in the processes to make the compound of formula (I) herein. Further, the starting materials are known or can be prepared by known methods.

Under certain circumstances as discussed above, it is necessary to protect either the N or O of intermediates. The examples above showing this noted process with suitable protecting groups which are known are not meant to be limiting. Introduction and removal of such suitable oxygen and nitrogen protecting groups are well-known in the art of organic chemistry; see for example "Protective Groups in Organic Chemistry," J. F. W. McOmie, *Advances in Organic Chemistry*, Vol. 3,191–281 (1963); R. A. Borssonas, *Advances in Organic Chemistry*, Vol. 3, 159–190 (1963); J. F. W. McOmie, *Chem. & Ind.*, 603 (1979), and T. W. Greene, "Protective Groups in Organic Synthesis", Wiley (New York) 1981, Chapters 2, 3, and 7.

Examples of suitable oxygen protecting groups are benzyl, t-butyldimethylsilyl, ethoxyethyl, methoxyethoxymethyl, and the like. Protection of an N—H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbony, vinyloxycarbamate acetyl, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The invention is further elaborated by the representative examples as follows. Such examples are not meant to be limiting.

Preparation 1

Methyl 2-[(2,6-dichloro-3-methylphenyl)amino]-benzoate

Oxalyl chloride (9.50 g, 74.8 mmol) in 20 ml of methylene chloride is added dropwise to a 0° C. suspension of meclomen (10.20 g, 34.4 mmol) and dimethylformamide (2.70 ml, 34.7 mmol) in 50 ml of methylene chloride. The clear yellow solution is stirred at 0° C. for 90 minutes then added by cannula to 110 ml of methanol at room temperature. The white suspension is stirred at room temperature overnight. The white solid is collected providing 7.52 g of product. The filtrate is concentrated and the residue partitioned between ethyl acetate and water. The organic layer is washed with brine, dried over magnesium sulfate and concentrated, providing an additional 2.45 g of product (94% total), mp 130°–131° C.

Analysis for $C_{15}H_{13}Cl_2NO_2$ requires: C, 58.08; H, 4.22; Cl, 22.86; N, 4.52 Found: C, 57.72; H, 4.13; Cl, 22.99; N, 4.38

Preparation 2

2-[(2,6-Dichloro-3-methylphenyl)amino]-benzoic acid, hydrazide

Hydrazine hydrate (2 ml) is added dropwise to a suspension of methyl 2-[(2,6-dichloro-3-methylphenyl)amino]-benzoate (227.1 mg, .73 mmol) in 10 ml of methanol. The reaction mixture is heated at 60° C. for seven hours under an atmosphere of nitrogen and then allowed to cool to room temperature overnight. The now clear colorless solution is concentrated in vacuo and chromatographed, eluting with ethyl acetate and hexane (gradient of 1:2 to 1:1), providing 208.6 mg (92%) of a white solid, mp 158°–160° C.

Analysis for $C_{14}H_{13}Cl_2N_3O$ requires: C, 54.21; H, 4.22; Cl, 22.86; N, 13.55 Found: C, 54.16; H, 4.20; Cl, 22.95; N, 13.44

EXAMPLE 1

5-[2-[2,6-Dichloro-3-methylphenyl)amino]phenyl]-1,3,4-oxadiazol- 2(3H)-one 1,1'-Carbonyldiimidazole (95.0 mg, 0.57 mmol) is added to a 0° C. solution of 2-[(2,6-dichloro-3-methylphenyl)amino]-benzoic acid, hydrazide (127.4 mg, 0.41 mmol) and triethylamine (60.0 µl, 0.43 mmol) in 10 ml of tetrahydrofuran. After stirring under nitrogen for five hours, additional triethylamine (40.0 µ) and 1,1'-carbonyldiimidazole (50.0 mg) are added and the reaction is allowed to warm to room temperature overnight. The volatiles are removed in vacuo and the residue dissolved in ether. The ether solution is washed consecutively with 1N hydrochloric acid, saturated sodium bicarbonate and brine. The organic layer is dried over sodium sulfate, filtered and concentrated in vacuo. The resultant white solid is purified by chromatography, eluting with hexane:ethyl acetate (2:1), to give 108.8 mg (79%) of product, mp 253°–254° C.

Anal. for $C_{15}H_{11}Cl_2N_3O_2$ requires: C, 53.59; H, 3.30; Cl, 21.09; N, 12.50 Found: C, 53.39; H, 3.45; Cl, 20.82; N, 12.15

EXAMPLE 2

5-[2-[(2,6-Dichloro-3-methylphenyl)amino]phenyl]-1,3,4-oxadiazol-2(3H)-thione 2-[(2,6-Dichloro-3-methylphenyl)amino]-benzoic acid, hydrazide (1.172 g, 3.78 mmol) is dissolved in 20 ml of methanol, and the solution is cooled to 0° C. Carbon disulfide (520 µl, 8.82 mmol) is added, followed by potassium hydroxide (266.0 mg, 4.03 mmol). The solution is heated at reflux for seven hours and allowed to cool to room temperature overnight. The solution is concentrated in vacuo and the residue dissolved in water. The aqueous solution is acidified with 1N hydrochloric acid and the resulting solids extracted into a 1:1 mixture of ether and ethyl acetate. The organic layer is dried over magnesium sulfate, filtered and concentrated in vacuo. The residue is chromatographed, eluting with hexane:ethyl acetate (2:1) providing 864.0 mg (65%) of product, mp 257°–259° C.

Anal. for $C_{15}H_{11}Cl_2N_3OS$ requires: C, 51.15; H, 3.15; Cl, 20.13; N, 11.93; S, 9.10 Found: C, 50.98; H, 3.20; Cl, 20.29; N, 11.88; S, 9.26

EXAMPLE 3

5-[2-[(2,6-Dichloro-3-methylphenyl)amino]phenyl]-1,3,4-oxadiazol-2(3H)-thione, sodium salt 570 µl of a 1N sodium hydroxide solution (0.57 mmol) is added dropwise to a 0° C. suspension of 5-[2-[(2,6-dichloro-3-methylphenyl)-amino]phenyl]-1,3,4-oxadiazol-2(3H)-thione (203.3 mg, 0.57 mmol) in 4 ml of methanol. The resulting clear solution is stirred at 0° C. for one hour and then concentrated in vacuo. The solid is dried under high vacuum at 60° C. for one hour and then at room temperature overnight, providing 220.8 mg (100%) of a glassy beige solid, mp is undefined.

Anal. for $C_{15}H_{10}Cl_2N_3OSNa-.5H_2O$ requires: C, 47.04; H, 2.90; Cl, 18.51; N, 10.97 Found: C, 47.05; H, 2.77; Cl, 18.87; N, 10.90

Preparation 3

2-[(2,6-Dichloro-3-methylphenyl)amino]-benzoic acid, 2-(aminothioxomethyl)hydrazide Oxalyl chloride (2.85 g, 22.5 mmol) in 10 ml of methylene chloride is added dropwise to a 0° C. suspension of meclofenamic acid (3.17 g, 10.6 mmol) and dimethylformamide (830 µl, 10.6 mmol) in 50 ml of methylene chloride. The clear yellow solution is stirred at 0° C. for 15 minutes and then at room temperature for 30 minutes. The solution is then concentrated in vacuo to give a yellow solid. This solid is added in portions to a suspension of thiosemicarbazide (1.95 g, 2.1 mmol) in 20 ml of pyridine. The suspension is stirred at 0° C. for 30 minutes then at room temperature overnight. The reaction mixture is concentrated in vacuo and the residue is partitioned between ethyl acetate and water. The organic layer is concentrated, then slurried with equal volumes of ethyl acetate and hexane. The off-white solid is collected by filtration providing 1.66 g (42%) of product, mp is undefined.

Anal. for $C_{15}H_{14}Cl_2N_4SO$ requires: C, 48.79; H, 3.82; N, 15.17; S, 8.68 Found: C, 48.39; H, 3.74; N, 15.45; S, 8.37

EXAMPLE 4

5-[2-[(2,6-Dichloro-3-methylphenyl)amino]phenyl]-1,3,4-thiadiazol-2-amine

Methanesulfonic acid (280 µl, 4.31 mol) is added dropwise to a suspension of 2-[(2,6-dichloro-3-methylphenyl)amino]-benzoic acid, 2-(aminothioxomethyl)hydrazide (1.008 g, 2.73 mmol) in 30 ml of toluene. The mixture is heated at reflux for three hours under a nitrogen atmosphere and allowed to cool to room temperature overnight. The tan solid is filtered off and suspended in 100 ml of ethyl acetate. The suspension is then stirred vigorously with 40 ml of 10% aqueous ammonium hydroxide, and the layers are separated. The ethyl acetate layer is washed with water, and dried over magnesium sulfate. Filtration and concentration in vacuo gives a white solid. Drying at 60° C. in vacuo overnight provides 560.8 mg (59%) of product, mp 219°–226° C.

Anal. for $C_{15}H_{12}Cl_2N_4S$ requires: C, 51.29; H, 3.44; Cl, 20.19; N, 15.95; S, 9.13 Found: C, 51.30; H, 3.51; Cl, 20.13; N, 16.04; S, 9.00

Preparation 4

2-[(2,6-Dichloro-3-methylphenyl)amino]-benzamide

Oxalyl chloride (1.90 g, 14.8 mmol) is added dropwise to a 0° C. suspension of meclofenamic acid (2.00 g, 6.7 mmol) and dimethylformamide (530 μl, 6.7 mmol) in 100 ml of methylene chloride. The clear yellow solution is stirred at 0° C. for one hour and then added by cannula to 3.6 ml of ammonium hydroxide (29% aqueous solution) in tetrahydrofuran at room temperature. After one hour the volatiles are removed and the residue partioned between ethyl acetate and water. The organic layer is washed with brine and dried over magnesium sulfate and concentrated. The white solid is recrystallized from ethyl acetate and isopropanol to give 1.30 g (69%), mp 185°–187° C.

Anal. for $C_{14}H_{12}Cl_2N_2O$ requires: C, 56.96; H, 4.11; N, 9.49 Found: C, 56.89; H, 4.04; N, 9.50

Preparation 5

2-[(2,6-Dichloro-3-methylphenyl)amino]-benzene thioamide

Phosphorous pentasulfide (1.27 g, 5.60 mmol) is added to a colorless solution of 2-[(2,6-dichloro-3-methylphenyl)amino]-benzamide (1.45 g, 4.90 mmol) in 20 m room temperature. The resulting mixture is stirred under nitrogen overnight. The white solids are removed by filtration and washed with tetrahydrofuran. The solution is concentrated in vacuo and chromatographed, eluting with hexane:ethyl acetate (3:1), providing 308.7 mg (20%) of a pale yellow solid, mp 134°–136° C.

Anal. for $C_{14}H_{12}Cl_2N_2S$ requires: C, 54.03; H, 3.89; Cl, 22.78; N, 9.00; S, 10.30 Found: C, 53.81; H, 3.73; Cl, 22.53; N, 8.81; S, 10.03

Alternative Preparation of 2-[(2,6-dichloro-3-methylphenyl)amino]-benzene thiomide Lawesson's Reagent (2.67 g, 6.60 mmol) is added to a colorless solution of 2-[(2,6-dichloro-3-methylphenyl)amino]-benzamide (2.83 g, 9.60 mmol) in 50 ml of tetrahydrofuran at room temperature. The resulting mixture is stirred under nitrogen for three days. The clear yellow solution is then heated at reflux for two hours. The solution is concentrated in vacuo and chromatographed, eluting with hexane:ethyl acetate (gradient of 6:1 to 3:1), providing 1.71 g (57%) of a pale yellow solid.

Preparation 6

2-[(2,6-Dichloro-3-methylphenyl)amino]-benzene carboximidic acid, hydrazide

Hydrazine hydrate (430 μl) is added dropwise to a room temperature solution of 2-[(2,6-dichloro-3-methylphenyl)amino]-benzene thioamide (1.71 g, 5.48 mmol) in 30 ml of methanol. The solution is stirred at room temperature under nitrogen for five hours, then concentrated in vacuo to half its original volume. This material is chromatographed, eluting with ethyl acetate:hexane (gradient of 1:1 to 3:1) to give 1.15 g (68%) of a glassy pale yellow solid. This material darkens and softens after two days at room temperature.

Anal. for $C_{14}H_{14}Cl_2N_4$ requires: C, 54.38; H, 4.56; N, 18.12 Found: C, 54.23; H, 4.70; N, 18.23

EXAMPLE 5

5-[2-[(2,6-Dichloro-3-methylphenyl)amino]phenyl]-1,3,4-thiadiazol-2 (3H)-thione Carbon disulfide (100 μl, 1.58 mmol) is added dropwise to a room temperature solution of 2-[(2,6-dichloro-3-methylphenyl)amino]benzene carboximidic acid hydrazide (183.4 mg, 0.595 mmol) in 5 ml of methanol. The solution is stirred under a nitrogen atmosphere at room temperature for two hours and then concentrated. The residue is purified by chromatography eluting with ethyl acetate:hexane (1:4) to give 107.0 mg (49%) of a yellow solid, mp 250°–252° C. with decomposition.

Anal. for $C_{15}H_{11}Cl_2N_3S_2$ requires: C, 48.92; H, 3.01; Cl, 19.25; N, 11.41 Found: C, 48.85; H, 3.07; Cl, 19.04; N, 11.26

Preparation 7

2-[(3-Trifluoromethylphenyl)amino]-benzoic acid, hydrazide

Hydrazine hydrate (14 ml) is added dropwise to a solution of methyl 2-[(3-trifluoromethylphenyl)amino]-benzoate (1.463 g, 4.95 mmol) in 70 ml of methanol. The reaction solution is heated at 60° C. under an inert atmosphere for two hours and then concentrated in vacuo and chromatographed, eluting with ethyl acetate and hexane (1:1), providing 763.0 mg (52%) of a white solid, mp 134°–135° C.

Anal. for $C_{14}H_{12}F_3N_3O$ requires: C, 56.95; H, 4.10; F, 19.30; N, 14.23 Found: C, 56.93; H, 4.21; F, 19.17; N, 14.18

EXAMPLE 6

5-[2-[[3-(Trifluoromethyl)phenyl]amino]phenyl]-1,3,4-oxadiazol-2(3H)-thione

Potassium hydroxide (123.0 mg, 1.87 mmol) is added to a 0° C. solution of 2-[(3-trifluoromethylphenyl)amino]-benzoic acid, hydrazide (515.8 mg, 1.75 mmol) and carbon disulfide (250 μl, 3.96 mmol) in 15 ml of methanol. The mixture is heated at reflux overnight. The solution is concentrated in vacuo and the residue dissolved in water. The resulting aqueous solution is acidified with 1N hydrochloric acid and the resulting solids extracted into a 1:1 mixture of ether and ethyl acetate. The organic layer is washed with brine, dried over magnesium sulfate, filtered and concentrated in vacuo. The residue is chromatographed, eluting with hexane:ethyl acetate (1:1), providing a white solid. Drying in vacuo at 65° C. overnight gives 406.4 mg (69%) of product, mp 211°–213° C.

Anal. for $C_{15}H_{10}F_3N_3OS$ requires: C, 53.40; H, 2.99; N, 12.46 Found: C, 53.48; H, 2.96; N, 12.28

EXAMPLE 7

5-[[2-[(2,6-Dichlorophenyl)amino]phenyl]methyl]-1,3,4-oxadiazol-2(3H)-thione Potassium hydroxide (363.0 mg, 5.50 mmol) is added to a 0° C. suspension of 2-[(2,6-dichlorophenyl)amino]benzeneacetic acid, hydrazide (1.556 g, 5.01 mmol) and carbon disulfide (700 μl, 11.87 mmol) in 30 ml of methanol. The mixture is heated at reflux overnight under an atmosphere of nitrogen. The solution is concentrated in vacuo and the residue dissolved in water. The resulting aqueous solution is acidified with 1N hydrochloric acid and the resulting solids extracted into a 1:1 mixture of ether and ethyl acetate. The organic layer is dried over magnesium sulfate, filtered and concentrated in vacuo. The residue is chromatographed, eluting with hexane:ethyl acetate (1:1), providing a white solid. Drying in vacuo at 65° C. for five days gives 1.22 g (65%) of product, mp 168°–170° C.

Anal. for $C_{15}H_{11}Cl_2N_3OS$ requires: C, 51.15; H, 3.15; Cl, 20.13; N, 11.93; S, 9.10 Found: C, 51.25; H, 3.01; Cl, 20.01; N, 11.63; S, 8.87

Preparation 8

Ethyl 3-[2-[(2,6-dichloro-3-methylphenyl)amino]-phenyl-2-propenoate (Carbethoxymethylene)-triphenylphosphorane (239 mg, 0.69 mmol) is added to a solution of aldehyde (180 mg, 0.64 mmol) in 3 ml of toluene. The solution is stirred at room temperature overnight under an inert atmosphere. An additional amount of (carbethoxymethylene)-triphenylphosphorane (208 mg) is added and the reaction mixture is heated at 50° C. for 90 minutes. The solution is then applied directly to a column, eluting with hexane and ethyl acetate (9:1) providing 211 mg (94%) of product, mp 86°–87° C.

Anal. for $C_{18}H_{17}Cl_2NO_2$ requires: C, 61.72; H, 4.89; Cl, 20.25; N, 4.00 Found: C, 61.62; H, 4.91; Cl, 20.42; N, 3.85

EXAMPLE 8

5-[2-[(2,3-Dimethylphenyl)amino]phenyl]-1,3,4-oxadiazol-2(3H)-one 1,1'-Carbonyldiimidazole (912.3 mg, 5.63 mmoles) is added to a 0° C. solution of 2-[(2,3-dimethylphenyl)amino]benzoic acid hydrazide (1.041 g, 4.08 mmoles) and triethylamine (608 µl, 4.36 mmoles) in 20 ml of tetrahydrofuran. The reaction is stirred at room temperature for one hour. The volatiles are removed in vacuo, and the residue is dissolved in 1:1 ethyl acetate/ether. The organic solution is washed consecutively with 1N hydrochloric acid, saturated aqueous sodium bicarbonate, and brine. The organic layer is dried over magnesium sulfate, filtered, and concentrated in vacuo. The resultant white solid is purified by flash chromatography with 1:1 hexane/ethyl acetate as eluant to give 968.8 mg (85%) of 5-[2-[(2,3-dimethylphenyl)amino]phenyl]-1,3,4-oxadiazol-2(3H)-one, mp 239°–241° C.

Anal. for $C_{16}H_{15}N_3O_2$ requires: C, 68.31; H, 5.38; N, 14.94 Found: C, 68.44; H, 5.36; N, 15.02

EXAMPLE 9

5-[2-[(2,3-Dimethylphenyl)amino]phenyl]-1,3,4-oxadiazole-2(3H)-thione

Carbon disulfide (572 µl, 9.48 mmoles) is added to a suspension of 2-[(2,3-dimethylphenyl)amino]-benzoic acid hydrazide (1.041 g, 4.08 mmoles) in 20 ml of methanol. Potassium hydroxide (286.0 mg, 4.34 mmoles) is added, and the mixture is heated at reflux overnight. The solution is concentrated in vacuo, and the residue is dissolved in water. The aqueous solution is acidified with 1N hydrochloric acid, and the resulting solids are extracted into ethyl acetate. The organic layer is dried over magnesium sulfate, filtered, and concentrated in vacuo. The residue is purified by flash chromatography with 2:1 hexane/ethyl acetate as eluant to give 964.0 mg (80%) of a white solid which is 5-[2-[(2,3-dimethylphenyl)amino]phenyl]-1,3,4-oxadiazole-2(3H)-thione, mp 242°–244° C. dec.

Anal. for $C_{16}H_{15}N_3OS$ requires: C, 64.62; H, 5.08; N, 14.13; S, 10.78 Found: C, 64.94; H, 5.16; N, 14.22; S, 10.48

EXAMPLE 10

2-[(3-Trifluoromethylphenyl)amino]-benzoic acid, 2-(aminothioxomethyl)hydrazide

N,N'-Carbonyldiimidazole (4.56 g, 27.6 mmoles) is added to a room temperature solution of flufenamic acid (5.07 g, 18.0 mmoles) in 70 ml of tetrahydrofuran. The clear yellow solution is stirred at room temperature for three hours. The solution is then added via cannula to a suspension of thiosemicarbazide (3.41 g, 37.5 mmoles) in 55 ml of pyridine. The suspension is heated at reflux overnight. The clear orange solution is concentrated in vacuo, and the residue is partitioned between ethyl acetate and water. The organic layer is washed with additional water, dried over magnesium sulfate, and concentrated. The resulting solid is slurried with a 1:3 mixture of ethyl acetate and hexane. The off-white solid is collected by filtration providing 2.80 g (44%) of 2-[(3-trifluoromethylphenyl)amino]-benzoic acid, 2-(aminothioxomethyl)hydrazide.

5-[2-[(3-Trifluoromethylphenyl)amino]phenyl]-1,3,4-thiadiazol-2-amine

Methanesulfonic acid (260 µl, 4.01 mmoles) is added dropwise to a suspension of 2-[(3-trifluoromethylphenyl)amino]-benzoic acid, 2-(aminothioxo-methyl)hydrazide (865.9 mg, 2.44 mmoles) in 30 ml of toluene. The mixture is heated at reflux for two hours. The solvent is decanted from the bright red oil. The oil is washed with toluene and stirred with ether to yield a red solid. The solid is filtered off and suspended in 50 ml of ethyl acetate. The suspension is stirred vigorously with 10% aqueous ammonium hydroxide and the layers are separated. The ethyl acetate layer is washed with water and dried over magnesium sulfate. Filtration and concentration in vacuo gives a light brown solid that is purified by flash chromatography eluting with a gradient of hexane and ethyl acetate (1:1 to 1:3) to provide 289.5 mg (35%) of 5-[2-[(3-trifluoromethylphenyl)amino] phenyl]-1,3,4-thiadiazol-2-amine, mp 122°–123° C.

Anal. for $C_{15}H_{11}F_3N_4S$ requires: C, 53.56; H, 3.30; N, 16.66; S, 9.53 Found: C, 53.53; H, 3.33; N, 16.65; S, 9.53

EXAMPLE 11

2-[(3-Trifluoromethylphenyl)amino]-benzene thioamide

Lawesson's Reagent (4.55 g, 11.26 mmoles) is added to a colorless solution of 2-[(3-trifluoromethylphenyl)amino]-benzamide (5.22 g, 18.64 mmoles) in 100 ml of tetrahydrofuran at room temperature. The resulting mixture is stirred under nitrogen for one hour, and then heated at reflux for 2.5 hours. The solution is concentrated in vacuo, and purified by flash chromatography with a gradient of 5:1 to 3:1 hexane/ethyl acetate as eluant, to provide 3.01 g (55%) of a bright yellow solid 2-[(3-trifluoromethylphenyl)amino]-benzene thioamide, mp 106°–108° C.

Anal. for $C_{14}H_{11}F_3N_2S$ requires: C, 56.74; H, 3.74; N, 9.46; S, 10.82 Found: C, 56.50; H, 3.83; N, 9.19; S, 10.68

EXAMPLE 12

2-[(3-Trifluoromethylphenyl)amino]-benzene carboximidic acid hydrazide

Hydrazine hydrate (1.80 ml) is added dropwise to a room temperature solution of 2-[(3-trifluoromethylphenyl)amino] benzene thioamide (2.88 g, 9.73 mmoles) in 100 ml of methanol. The solution is stirred at room temperature under nitrogen for six hours. An additional 400 µl of hydrazine hydrate is added, and stirring is continued for one hour. The solution is concentrated in vacuo and purified by flash chromatography eluting with ethyl acetate to give 2.28 g (80%) of a gummy tan solid. This material is used immediately in the next reaction.

5-[2-[(3-Trifluoromethylphenyl)amino]phenyl]-1,3,4-thiadiazole-2(3H)-thione

Carbon disulfide (160 µl, 2.65 mmoles) is added dropwise to a solution of 2-[(3-trifluoromethylphenyl)amino]benzene carboximidic acid hydrazide (247.1 mg, 0.840 mmoles) as prepared above in 6 ml of methanol. The solution is stirred at ambient temperature for two hours and then concentrated. The residue is purified by flash chromatography eluting with ethyl acetate:hexane (1:4) to give 160.1 mg (54%) of a yellow solid which is 5-[2-[(3-trifluoromethylphenyl)amino]phenyl]-1,3,4-thiadiazole-2(3H)-thione, mp 225°–227° C.

Anal. for $C_{15}H_{10}F_3N_3S_2$ requires: C, 50.98; H, 2.85; N, 11.89; S, 18.15 Found: C, 50.59; H, 2.51; N, 11.78; S, 17.79

EXAMPLE 13

5-[2-[(3-Trifluoromethylphenyl)amino]phenyl]-1,3,4-oxadiazole-2(3H)-thione, sodium salt 3.66 ml of a 1N sodium hydroxide solution (3.66 mmoles) is added dropwise to a 0° C. suspension of 5-[2-[(3-trifluoromethylphenyl)-amino]-phenyl]- 1,3,4-oxadiazole-2(3H)-thione (1.236 g, 3.66 mmoles) in 12 ml of methanol. The resulting clear solution is stirred at 0° C. for 90 minutes and then concentrated in vacuo. The solid is dissolved in water, and the solution concentrated in vacuo. The white solid is dried under high vacuum at 70° C. overnight providing 1.069 g (81%) of 5-[2-[(3-trifluoromethylphenyl)amino] phenyl]-1,3,4-oxadiazole-2(3H)-thione, sodium salt, mp 223°–226° C.

Anal. for $C_{15}H_9F_3N_3OSNa-.5H_2O$ requires: C, 48.91; H, 2.74; N, 11.41 Found: C, 48.70; H, 2.51; N, 11.18

EXAMPLE 14

5-[2-[(3-Trifluoromethylphenyl)amino]phenyl]-1,3,4-oxadiazole-2(3H)-thione, choline salt A 46.6% solution of aqueous choline bicarbonate (995.2 mg, 2.81 mmoles) is added dropwise to a warm suspension of 5-[2-[(3-trifluoromethylphenyl)-amino]phenyl]-1,3,4-oxadiazole-2(3H)-thione (968.5 mg, 2.87 mmoles) in 10 ml of methanol. The resulting pale yellow solution is heated at reflux for two hours followed by stirring at room temperature overnight. The reaction mixture is concentrated in vacuo, and the residue is recrystallized from acetone and t-butyl methyl ether. The white solid is dried under vacuum at 50° C. overnight, providing 1.035 g (82%) of 5-[2-[(3-trifluoromethylphenyl)amino]phenyl]-1,3,4-oxadiazole-2(3H)-thione, choline salt, mp 103°–104° C.

Anal. for $C_{20}H_{23}F_3N_4O_2S$ requires: C, 54.53; H, 5.26; N, 12.72; S, 7.28 Found: C, 54.58; H, 5.24; N, 12.75; S, 7.08

EXAMPLE 15

5-[2-[(3-Trifluoromethylphenyl)amino]phenyl]-1,3,4-thiadiazole- 2(3H)-thione, choline salt A 46.6% solution of aqueous choline bicarbonate (830.0 mg, 2.34 mmoles) is added dropwise to a warm suspension of 5-[2-[(3-trifluoromethylphenyl)-amino]phenyl]-1,3,4-thiadiazole-2(3H)-thione (831.0 mg, 2.35 mmoles) in 20 ml of methanol. The resulting clear solution is heated at reflux for 90 minutes and then stirred at room temperature overnight. The reaction mixture is concentrated in vacuo, and the residue is recrystallized from acetone and t-butyl methyl ether. The white solid is dried under vacuum at 50° C. overnight, then at 60° C. overnight, providing 773.0 mg (72%) of 5-[2-[(3-trifluoromethylphenyl)amino]phenyl]-1,3,4-thiadiazole-2(3H)-thione, choline salt, mp 140.5°–142° C.

Anal. for $C_{20}H_{23}F_3N_4OS_2$ requires: C, 52.61; H, 5.08; N, 12.27 Found: C, 52.39; H, 5.07; N, 12.27

EXAMPLE 16

5-[2-[[3-(Trifluoromethyl)phenyl]amino]phenyl]-1,3,4-oxadiazol- 2-amine

To a room temperature solution of 2-[(3-trifluoromethylphenyl)amino]benzoic acid hydrazide (532.7 mg, 1.81 mmoles) in 5 ml of dioxane is added sodium bicarbonate (155.0 mg, 1.84 mmoles) in 5 ml of water. After stirring at room temperature for five minutes, cyanogen bromide (192.0 mg, 1.81 mmoles) is added, and stirring is continued for 2.5 hours. The tan precipitate is removed by filtration and washed with 10 ml of 50% aqueous dioxane. Drying in vacuo provides 398.0 mg (69%) of 5-[2-[[3-(trifluoromethyl)phenyl]amino]phenyl]-1,3,4-oxadiazol-2-amine, mp 185°–187° C.

Anal. for $C_{15}H_{11}F_3N_4O$ requires: C, 56.25; H, 3.46; N, 17.49 Found: C, 56.35; H, 3.46; N, 17.74

EXAMPLE 17

5-[2-[[2,6-Dichloro-3-methylphenyl]amino]phenyl]-1,3,4-oxadiazol- 2-amine

To a room temperature solution of 2-[2,6-dichloro-3-methylphenyl)amino]-benzoic acid hydrazide (1.936 g, 6.24 mmoles) in 20 ml of dioxane is added sodium bicarbonate (523.5 mg, 6.23 mmoles) in 15 ml of water. After stirring at room temperature for five minutes, cyanogen bromide (675.0 mg, 6.37 mmoles) is added, and stirring is continued for three hours. The tan precipitate is collected by filtration. This material is stirred with ethyl acetate, filtered, and the solid is dried in vacuo to yield 1.3698 g (65%) of 5-[2-[[2,6-dichloro-3-methylphenyl]amino]phenyl]-1,3,4-oxadiazol-2-amine, mp 255°–257° C.

Anal. for $C_{15}H_{12}Cl_2N_4O$ requires: C, 53.74; H, 3.61; Cl, 21.16; N, 16.72 Found: C, 53.60; H, 3.51; Cl, 21.46; N, 16.73

EXAMPLE 18

2,6-Dichloro-3-methyl-N-[2-(1,3,4-oxadiazol-2-yl)phenyl]benzenamine

To a room temperature suspension of 2-[(2,6-dichloro-3-methylphenyl)amino]-benzoic acid hydrazide (355.1 mg, 1.15 mmoles) in 6 ml of ethanol is added 2 ml of triethyl orthoformate followed by p-toluenesulfonic acid (20 mg, 0.11 mmoles). After stirring at room temperature overnight, the clear yellow solution is concentrated in vacuo. The residue is subjected to flash chromatography eluting with hexane:ethyl acetate (3:1). Subsequent recrystallization from ethanol yields 244.1 mg (67%) of 2,6-dichloro-3-methyl-N-[2-( 1,3,4-oxadiazol-2-yl)phenyl]benzenamine, mp 180°–181° C.

Anal. for $C_{15}H_{11}Cl_2N_3O$ requires: C, 56.27; H, 3.46; Cl, 22.15; N, 13.12 Found: C, 56.47; H, 3.51; Cl, 21.88; N, 13.08

EXAMPLE 19

2,6-Dichloro-3-methyl-N-[2-[5-(methylthio)-1,3,4-oxadiazol-2-yl]phenyl]benzenamine To a room temperature suspension of 5-[2-[(2,6-dichloro-3-methylphenyl)amino]phenyl]-1,3,4-oxadiazole-2(3H)-thione (1.706 g, 4.85 mmoles) in 70 ml of methanol is added dropwise 5.0 ml of 1.0N sodium hydroxide. The clear pale yellow solution is stirred at room temperature for 10 minutes. Iodomethane (320.0 µl, 5.13 mmoles) is added dropwise, and stirring is continued for six hours. The white solid is collected by filtration and dried in vacuo overnight at 60° C. to provide 1.530 g (86) of 2,6-dichloro-3-methyl-N-[2-[5-(methylthio)-1,3,4-oxadiazol-2-yl]phenyl]benzenamine, mp 170°–171° C.

Anal. for $C_{16}H_{13}Cl_2N_3OS$ requires: C, 52.47; H, 3.58; Cl, 19.36; N, 11.47; S, 8.75 Found: C, 52.07; H, 3.51; Cl, 19.27; N, 11.45; S, 8.96

EXAMPLE 20

2,6-Dichloro-3-methyl-N-[2-[5-(methylsulfonyl)-1,3,4-oxadiazol-2-yl]phenyl]benzenamine To a 0° C. solution of 2,6-dichloro-3-methyl-N-[2-[5-(methylthio)-1,3,4-oxadiazol-2-yl]phenyl]benzenamine (514.8 mg, 1.41 mmoles) in 30 ml of methylene chloride is added sodium bicarbonate (601.0 mg, 7.15 mmoles), followed by m-chloroperbenzoic acid (803.0 mg, 3.73 mmoles). The reaction mixture is stirred at 0° C. for two hours, then at room temperature overnight. An additional amount of m-chloroperbenzoic acid (75.0 mg) is added, and stirring is continued for six hours. The mixture is poured into methylene chloride and washed with aqueous saturated sodium bicarbonate followed by water. The organic layer is dried over magnesium sulfate, and concentrated in vacuo. The residue is purified by flash chromatography eluting with hexane:ethyl acetate (3:1) to provide 327.8 mg (59%) of a light tan solid which is 2,6-dichloro-3-methyl-N-[2-[5-(methylsulfonyl)-1,3,4-oxadiazol-2-yl]phenyl]benzenamine, mp 165°–169° C.

Anal. for $C_{16}H_{13}Cl_2N_3O_3S$ requires: C, 48.25; H, 3.29; N, 10.55; S, 8.05 Found: C, 48.39; H, 3.56; N, 10.40; S, 8.10

EXAMPLE 21

2,6-Dichloro-3-methyl-N-[2-[5-(methylsulfinyl)-1,3,4-oxadiazol- 2-yl]phenyl]benzenamine To a 0° C. solution of 2,6-dichloro-3-methyl-N-[2-[5-(methylthio)-1,3,4-oxadiazol-2-yl]phenyl]benzenamine (283.6 mg, 0.77 mmoles) in 10 ml of methylene chloride is added m-chloroperbenzoic acid (132.0 mg, 0.61 mmoles). The reaction mixture is stirred at 0° C. for one hour. An additional amount of m-chloroperbenzoic acid (33.0 mg, 0.15 mmoles) is added, and stirring is continued for one hour. The mixture is poured into methylene chloride and washed with saturated aqueous sodium bicarbonate followed by water. The organic layer is dried over magnesium sulfate and concentrated in vacuo. The residue is purified by flash chromatography eluting with hexane:ethyl acetate (1:1) to provide 220.1 mg (74%) of a white solid which is 2,6-dichloro-3-methyl-N-[2-[5-(methylsulfinyl)-1,3,4-oxadiazol-2-yl]phenyl]benzenamine, mp 146°–149° C.

Anal. for $C_{16}H_{13}Cl_2N_3O_2S$ requires: C, 50.27; H, 3.43; Cl, 18.55; N, 10.99; S, 8.39 Found: C, 50.33; H, 3.76; Cl, 18.33; N, 10.85; S, 8.38

EXAMPLE 22

5-[2-](2,6-Dichloro-3-methylphenyl)amino]phenyl]-1,3,4-oxadiazol- 2-yl-guanidine monohydrochloride To a solution of potassium tert-butoxide (111.3 mg, 0.99 mmoles) in 15 ml of tert-butyl alcohol is added guanidine hydrochloride (108.2 mg, 1.13 mmoles). The reaction mixture is stirred at room temperature for 10 minutes, then 2,6-dichloro-3-methyl-N-[2-[5-(methylsulfinyl)-1,3,4-oxadiazol-2-yl]phenyl]benzenamine (201.0 mg, 0.526 mmoles) is added, and the reaction mixture is heated at reflux for five minutes. The mixture is concentrated in vacuo. 20 ml of methanol is added to the residue followed by 100 ml of water. The resultant solid is collected by filtration and dissolved in 10% methanol in ethyl acetate. 50 ml of ether is added, followed by a few drops of saturated etheral hydrochloric acid. The white solid is collected and washed with ether to provide 154.4 mg (71%) of 5-[2-[(2,6-dichloro-3-methylphenyl)amino]phenyl]-1,3,4-oxadiazol-2-yl-guanidine monohydrochloride, mp 245°–248° C.

Anal. for $C_{16}H_{15}Cl_2N_6O \cdot .5H_2O$ requires: C, 4.46; H, 3.82; N, 19.88 Found: C, 44.67; H, 3.77; N, 19.68

EXAMPLE 23

5-[2-[(2,6-Dichloro-3-methylphenyl)amino]phenyl]-1,3,4-oxadiazol- 2-yl-cyanamide To a suspension of 2-[(2,6-dichloro-3-methylphenyl)amino]-benzoic acid hydrazide (394.1 mg, 1.27 mmoles) in 20 ml of 2-propanol is added triethylamine (200 µl, 1.43 mmoles) followed by diphenyl cyanocarbonimidate (371.9 mg, 1.56 mmoles). After 1.5 hours the resultant yellow solution is concentrated in vacuo. The residue is dissolved in 10 ml of ethyl acetate and partitioned between water and a 1:1 mixture of ether and hexane. The aqueous layer is acidified with 1N hydrochloric acid, and the resultant white solid is collected by filtration to provide 99.3 mg (22%) of 5-[2-[(2,6-dichloro-3-methylphenyl)amino]phenyl]-1,3,4-oxadiazol-2-yl-cyanamide, mp above 215° C.

Anal. for $C_{16}H_{11}Cl_2N_5O$ requires: C, 53.35; H, 3.08; N, 19.44 Found: C, 53.21; H, 2.81; N, 19.57

EXAMPLE 24

N-[2-[5-(Methylthio)-1,3,4-oxadiazol-2-yl]phenyl]-3-trifluoromethyl benzenamine To a room temperature solution of 5-[2-[(3-trifluoromethylphenyl)amino]phenyl]-1,3,4-oxadiazole-2(3H)-thione (1.130 g, 3.35 mmoles) in 40 ml of methanol is added dropwise 3.4 ml of 1.0N sodium hydroxide. The clear pale yellow solution is stirred at room temperature for 10 minutes. Iodomethane (220.0 µl, 3.53 mmoles) is added dropwise, and stirring is continued for four hours. The reaction mixture is concentrated in vacuo and the residue is partitioned between ethyl acetate and water. The organic layer is washed with additional water, dried over magnesium sulfate, and concentrated in vacuo. The solid is purified by flash chromatography eluting with hexane:ethyl acetate (4:1) to provide 1.011 g (86%) of a fluffy pale yellow solid which is N-[2-[5-(methylthio)-1,3,4-oxadiazol-2-yl]phenyl]-3-trifluoromethyl benzenamine, mp 94°–95° C.

Anal. for $C_{16}H_{12}F_3N_3OS$ requires: C, 54.69; H, 3.45; N, 11.96; S, 9.13 Found: C, 54.88; H, 3.47; N, 12.07; S, 8.94

EXAMPLE 25

N-[2-[5-(Methylsulfonyl)-1,3,4-oxadiazol-2-yl]phenyl]-3-trifluoromethyl benzenamine To a 0° C. solution of N-[2-[5-(methylthio)-1,3,4-oxadiazol-2-yl]phenyl]-3-trifluoromethyl benzenamide (1.284 g, 3.65 mmoles) in 60 ml of methylene chloride is added sodium bicarbonate (1.668 g, 19.85 mmoles), followed by m-chloroperbenzoic acid (2.015 g, 9.37 mmoles). The reaction mixture is stirred at 0° C. for one hour then at room temperature overnight. An additional amount of m-chloroperbenzoic acid (480 mg) and of sodium bicarbonate (332 mg) is added, and stirring is continued for six hours. The mixture is then poured into methylene chloride and washed with saturated aqueous sodium bicarbonate, followed by water. The organic layer is dried over magnesium sulfate, and concentrated in vacuo. The residue is purified by flash chromatography eluting with hexane:ethyl acetate (3:1) to provie 555.0 mg (40%) of a light yellow solid which is N-[2-[5-(methylsulfonyl)-1,3,4-oxadiazol-2-yl]phenyl]-3-trifluoromethyl benzenamine, mp 144°–148° C.

Anal. for $C_{16}H_{12}F_3N_3O_3S$ requires: C, 50.13; H, 3.16; N, 10.96; S, 8.36 Found: C, 50.06; H, 3.19; N, 10.67; S, 8.14

EXAMPLE 26

5-[2-[[3-(Trifluoromethyl)phenyl]amino]phenyl]-1,3,4-oxadiazol-2-yl-cyanamide To an ambient solution of N-[2-[5-(methylsulfonyl)-1,3,4-oxadiazol-2-yl]phenyl]-3-trifluoromethyl benzenamide (210.4 mg, 0.549 mmoles) in 5 ml of dimethylformamide is added 1 ml of water followed by cyanamide (196.0 mg, 4.66 mmoles) and triethylamine (100 µl, 0.717 mmoles). The reaction mixture is stirred at 80° C. overnight. An additional amount of cyanamide (96 mg) is added, and heating is continued for six hours. The mixture is poured into ether and extracted into 0.3N sodium hydroxide. The aqueous layer is acidified with 1N hydrochloric acid, and the resulting white solid is collected by filtration, washing with water. Recrystallization from acetonitrile provides 95.8 mg (51%) of 5-[2-[[3-(trifluoromethyl)phenyl]amino]phenyl]-1,3,4-oxadiazol-2-yl-cyanamide, mp above 230° C.

Anal. for $C_{16}H_{10}F_3N_5O$ requires: C, 55.65; H. 2.92; F, 16.51; N, 20.29 Found: C, 55.57; H, 2.60; F, 16.86; N, 20.25

EXAMPLE 27

5-[2-[[3-(Trifluoromethyl)phenyl]amino]phenyl]-1,3,4-oxadiazol- 2-yl-guanidine hydrochloride Sodium metal (42.0 mg, 1.82 mmoles) is added to 5 ml of tert-butanol and the reaction mixture is heated to 80° C. Guanidine hydrochloride (200.2 mg, 2.09 mmoles) is added, and the thick precipitate is stirred at room temperature for 25 minutes. N-[2-[5-(methylsulfonyl)-1,3,4-oxadiazol-2-yl]phenyl]-3-trifluoromethyl benzenamine (202.3 mg, 0.53 mmoles) is added, and the mixture is heated at 80° C. for 1.5 hours. Additional guanidine hydrochloride (108.0 mg, 1.13 mmoles) and potassium tert-butoxide (112.0 mg, 1.00 mmoles) are added and heating is continued for one hour. After cooling, the solids are washed with methanol and water is added to the filtrate. The resultant white solid is collected by filtration and dissolved in ether. A few drops of ether saturated with hydrochloric acid are added to the etheral solution, resulting in the formation of a thick white precipitate. This solid is collected by filtration and washed with ether to provide 138.7 mg (66%). An analytical sample is obtained by recrystallization from ethanol and ether which is 5-[2-[[3-(trifluoromethyl)phenyl]amino]phenyl]-1,3,4-oxadiazol-2-yl-guanidine hydrochloride, mp 224°–226° C.

Anal. for $C_{16}H_{14}ClF_3N_6O$ requires: C, 48.19; H, 3.54; N, 21.08 Found: C, 48.00; H, 3.36; N, 20.81

EXAMPLE 28

2,6-Dichloro-3-methyl-N-[2-[5-(methylthio)-1,3,4-thiadiazol- 2-yl]phenyl]benzenamine To a 0° C. suspension of 2-[(2,6-dichloro-3-methylphenyl)amino]-benzoic acid hydrazide (1.010 g, 3.25 mmoles) in 25 ml of methanol is added carbon disulfide (200 µl, 3.32 mmoles), followed by potassium hydroxide (220.0 mg, 3.34 mmoles). The reaction mixture is stirred at 0° C. for 30 minutes, then at room temperature for five hours. Iodomethane (220.0 µl, 3.53 mmoles) is added and stirring is continued overnight. The solution is concentrated in vacuo and partitioned between ethyl acetate and water. The organic layer is washed with saturated aqueous sodium bicarbonate, dried over magnesium sulfate, and concentrated in vacuo. The residue is purified by flash chromatography with 2:1 hexane/ethyl acetate as eluant to provide 730.3 mg (56%) of product.

A solution of the above solid (680.2 mg, 1.70 mmoles) and p-toluenesulfonic acid (375.0 mg, 1.97 mmoles) in 20 ml of toluene is heated at reflux for two hours. The solution is concentrated in vacuo and the residue is subjected to flash chromatography eluting with hexane:ethyl acetate (10:1). The resultant material is stirred with hexane and filtered to give 387.4 mg (60%) of a white solid which is 2,6-dichloro-3-methyl-N-[2-[5-(methylthio)-1,3,4-thiadiazol-2-yl]phenyl]benzenamine, mp 162°–165° C.

Anal. for $C_{16}H_{13}Cl_2N_3S_2$ requires: C, 50.26; H, 3.43; Cl, 18.55; N, 10.99 Found: C, 50.20; H, 3.38; Cl, 18.76; N, 10.95

EXAMPLE 29

2,6-Dichloro-3-methyl-N-[2-[5-(methylsulfinyl)-1,3,4-thiadiazol- 2-yl]phenyl]benzenamine To a 0° C. solution of 2,6-dichloro-3-methyl-N-[2-[5-(methylthio)-1,3,4-thiadiazol-2-yl]phenyl]benzenamine (1.435 mg, 3.75 mmoles) in 50 ml of methylene chloride is added m-chloroperbenzoic acid (898.0 mg, 4.17 mmoles).

The reaction mixture is stirred at 0° C. for one hour. The mixture is poured into methylene chloride and washed with saturated aqueous sodium bicarbonate followed by water. The organic layer is dried over magnesium sulfate and concentrated in vacuo. Trituration with ethyl acetate followed by hexane, provides 1.223 g of a pale yellow solid. The filtrate is concentrated and purified by flash chromatography eluting with hexane:ethyl acetate (3:1) to provide an additional 120.5 mg (90% total yield) of 2,6-dichloro-3-methyl-N-[2-[5-(methylsulfinyl)-1,3,4-thiadiazol-2-yl]phenyl]benzenamine, mp 158°–160° C.

Anal. for $C_{16}H_{13}Cl_2N_3OS_2$ requires: C, 48.24; H, 3.29; Cl, 17.80; N, 10.55 Found: C, 48.16; H, 3.24; Cl, 17.43; N, 10.30

EXAMPLE 30

3-Trifluoromethyl-N-[2-[5-(methylthio)-1,3,4-thiadiazol-2-yl]phenyl]benzenamine

To a 0° C. solution of 2-[(3-trifluoromethylphenyl)amino]-benzoic acid hydrazide (6.582 g, 22.31 mmoles) in 140 ml of methanol is added carbon disulfide (1.35 ml, 22.35 mmoles) followed by potassium hydroxide (1.351 g, 19.30 mmoles). The reaction mixture is stirred at 0° C. for two hours then at room temperature for three hours. Iodomethane (1.36 ml, 21.80 mmoles) is added, and stirring is continued overnight. The solution is concentrated in vacuo and partitioned between water and 1:1 hexane:ethyl acetate. The organic layer is washed with saturated aqueous sodium bicarbonate, dried over magnesium sulfate, and concentrated in vacuo. The residue is purified by flash chromatography eluting with hexane:ethyl acetate (2:1) to provide 5.89 g of product.

A solution of the above solid (5.86 g, 15.22 mmoles) in 85 ml of toluene is treated with p-toluene-sulfonic acid (3.30 g, 17.35 mmoles), and the reaction mixture is heated at reflux for 30 minutes. The white solid is removed by filtration washing with toluene. The filtrate is concentrated in vacuo, and the residue is subjected to flash chromatography eluting with hexane:ethyl acetate (5:1). The solid is stirred with hexane:ethyl acetate (3:1) and collected by filtration to give 2.525 g (45%) of a light yellow solid which is 3-trifluoromethyl-N-[2-[5-(methylthio)-1,3,4-thiadiazol-2-yl]phenyl]benzenamine, mp 86°–88° C.

Anal. for $C_{16}H_{12}F_3N_3S_2$ requires: C, 52.30; H, 3.29; N, 11.44 Found: C, 51.90; H, 3.28; N, 11.26

EXAMPLE 31

3-Trifluoromethyl-N,[2-[5-(methylsulfinyl)-1,3,4-thiadiazol-2-yl] phenyl]benzenamide mCBPA (654 mg, 3.04 mmoles) is added to a 0° C. solution of 3-trifluoromethyl-N-[2-[5-(methylthio)-1,3,4-thiadiazol-2-yl]phenyl]benzenamide (1.012 g, 2.75 mmoles) in 40 ml of methylene chloride. The suspension is stirred at 0° C. for one hour then poured into methylene chloride and washed with saturated $NaHCO_3$, followed by water. The organic layer is dried over magnesium sulfate, filtered and concentrated in vacuo. The residue is dissolved in 10 ml of 1:1 hexane:ethyl acetate and diluted with 150 ml of hexane. The bright yellow solid is collected by filtration to give 785 mg. This material is chromatographed, eluting with a gradient of 6:1 to 1:1 hexane:ethyl acetate to provide 569 mg (54%) of 3-trifluoromethyl-N-[2-[5-(methylsulfinyl)-1,3,4-thiadiazol-2-yl]phenyl]benzenamide, mp 125°–126° C.

Anal. for $C_{16}H_{12}F_3N_3OS_2$ requires: C, 50.12; H, 3.16; N, 10.96; S, 16.72 Found: C, 50.20; H, 3.38; N, 11.13; S, 16.80

EXAMPLE 32

5-[2-[(3-Trifluoromethylphenyl)amino]phenyl]-1,3,4-thiadiazol- 2(3H)-one

To a bright yellow solution of 3-trifluoromethyl-N-[2-[5-(methylsulfinyl)-1,3,4-thiadiazol-2-yl]phenyl]benzenamide (290.7 mg, 0.76 mmoles) in 10 ml of ethanol is added 5 ml of 1N NaOH. A bright red solution forms, followed by the formation of a thick tan precipitate. The mixture is stirred at room temperature overnight. The solid is collected by filtration and the filtrate is extracted with ethyl acetate. The organic layer is dried over magnesium sulfate, filtered and concentrated in vacuo. The solids are combined and dissolved in 3 ml of ethanol. 10 ml of 1N HCl is added and the solution is heated at reflux for four hours. After cooling to room temperature the light yellow solid is collected by filtration. The filtrate is extracted with ethyl acetate. The organic layer is dried over magnesium sulfate, filtered and concentrated in vacuo. The solids are combined and chromatographed eluting with 3:1 hexane :ethyl acetate to give 103.3 mg (40%) of 5-[2-[(3-trifluoromethylphenyl)amino]phenyl]-1,3,4-thiadiazol-2(3H)-one, mp 157°–160° C.

Anal. for $C_{15}H_{10}F_3N_3OS$ requires: C, 53.41; H, 2.99; N, 12.46; S, 9.50 Found: C, 53.52; H, 3.00; N, 12.32; S, 9.47

EXAMPLE 33

5-[2-[[3-(Trifluoromethyl)phenyl]amino]phenyl]-1,3,4-thiadiazol- 2-yl-guanidine hydrochloride To a room temperature solution of potassium t-butoxide (262 mg, 2.34 mmoles) in 15 ml of t-butanol is added guanidine hydrochloride (256 mg, 2.68 mmoles). The precipitate is stirred at room temperature for 10 minutes. 3-Trifluoromethyl-N-[2-[5-(methylsulfinyl)-1,3,4-thiadiazol-2-yl]phenyl]benzenamide (431.1 mg, 1.13 mmoles) is added, and the mixture is briefly heated at reflux. After cooling, the reaction mixture is partitioned between ether and water. The ether layer is dried over magnesium sulfate and filtered. A few drops of methanol saturated with hydrochloric acid are added to the etheral solution, resulting in the formation of a thick white precipitate. This solid is collected by filtration and washed with ether to provide 279.3 mg (60%) of 5-[2-[[3-(trifluoromethyl)phenyl]amino]phenyl]-1,3,4-thiadiazol-2-yl-guanidine hydrochloride, mp 247°–249° C.

Anal. for $C_{16}H_{14}ClF_3N_6S\cdot.5H_2O$ requires: C, 45.34; H, 3.56; N, 19.83 Found: C, 44.98; H, 3.20; N, 19.76

EXAMPLE 34

5-[2-[(2,6-Dichloro-3-methylphenyl)amino] phenyl]-1,3,4-thiadiazol- 2-yl-guanidine hydrochloride To a room temperature solution of potassium t-butoxide (302.7 mg, 2.70 mmoles) in 20 ml of t-butanol is added guanidine hydrochloride (281.1 mg, 2.94 mmoles). The precipitate is stirred at room temperature for 10 minutes. 2,6-Dichloro-3-methyl-N-[2-[5-(methylsulfinyl)-1,3,4-thiadiazol-2-yl]phenyl]benzenamide (511.6 mg, 1.29 mmoles) is added, and the mixture is briefly heated at reflux. After cooling, the reaction mixture is partitioned between ether and water. The ether layer is washed with brine, dried over magnesium sulfate and filtered. A few drops of methanol saturated with hydrochloric acid are added to the etheral solution. After standing at room temperature for two hours, the thick white precipitate is collected by filtration and washed with ether to provide 332.6 mg (60%) of 5-[2-[(2, 6-dichloro-3-methylphenyl)amino]phenyl]-1,3,4-thiadiazol-2-yl-guanidine hydrochloride, mp >280° C.

Anal. for $C_{16}H_{15}Cl_3N_6S$ requires: C, 44.71; H, 3.52; N, 19.56 Found: C, 44.92; H, 3.62; N, 19.47

What is claimed is:

1. A compound of the formula (II)

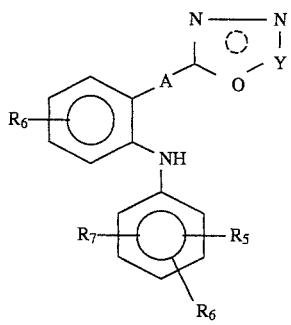

and a pharmaceutically acceptable salt thereof; wherein

A is a bond, $CH_2$ or $CH=CH$;

Y is (1) C—$SR_1$ wherein $R_1$ is H or lower alkyl,

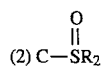

wherein $R_2$ is lower alkyl,

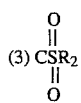

wherein $R_2$ is as defined above, (4) C—$NR_1R_3$ wherein $R_1$ is independently as defined above and $R_3$ is hydrogen or lower alkyl, (5) $CR_4$ wherein $R_4$ is lower alkyl, halogen, $CF_3$, $CO_2R_1$, or

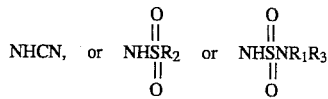

wherein $R_1$, $R_2$, and $R_3$ are independently as defined above;

$R_5$, $R_6$, and $R_7$ are independently lower alkyl, fluoro, chloro, bromo, iodo, trifluoromethyl, CN, hydroxy, lower alkoxy, —S(O)$_n$-lower alkyl wherein n is an integer of 0 through 2, $NO_2$ or $NR_9R_{10}$ wherein $R_9$ and $R_{10}$ are independently H, lower alkyl, or acyl;

and $R_8$ is hydrogen, lower alkyl, fluoro, chloro, bromo, iodo, trifluoromethyl, CN, hydroxy, lower alkoxy, —S(O)$_n$-lower alkyl wherein n is an integer of 0 through 2, $NO_2$ or $NR_9R_{10}$ wherein $R_9$ and $R_{10}$ are independently H, lower alkyl, or acyl.

2. A compound of claim 1 wherein A is a bond.
3. A compound of claim 1 wherein A is $CH_2$.
4. A compound of claim 1 wherein A is CH=CH.
5. A compound of claim 1 wherein Y is $CSR_1$, wherein $R_1$ is as defined above.
6. A compound of claim 1 wherein Y is

wherein $R_2$ is lower alkyl.

7. A compound of claim 1 wherein Y is

wherein $R_2$ is lower alkyl.

8. A compound of claim 1 wherein Y is $CNR_1R_3$.
9. A compound of claim 1 wherein Y is $CR_4$.
10. A compound of claim 1 which is 5-[[2-[(2,6-dichlorophenyl)amino]phenyl]methyl]-1,3,4-oxadiazol-2(3H)-thione.
11. A compound of claim 1 which is 5-[2-[[3-(trifluoromethyl)phenyl]amino]phenyl]-1,3,4-oxadiazol-2-amine.
12. A compound of claim 1 which is 5-[2-[[2,6-dichloro-3-methylphenyl]amino]phenyl]-1,3,4-oxadiazol-2-amine.
13. A compound of claim 1 which is 2,6-dichloro-3-methyl-N-[2-(1,3,4-oxadiazol-2-yl)phenyl]benzenamine.
14. A compound of claim 1 which is 2,6-dichloro-3-methyl-N-[2-[5-(methylthio)-1,3,4-oxadiazol-2-yl]phenyl]benzenamine.
15. A compound of claim 1 which is 2,6-dichloro-3-methyl-N-[2-[5-(methylsulfonyl)-1,3,4-oxadiazol-2-yl]phenyl]benzenamine.
16. A compound of claim 1 which is 2,6-dichloro-3-methyl-N-[2-[5-(methylsulfinyl)-1,3,4-oxadiazol-2-yl]phenyl]benzenamine.
17. A compound of claim 1 which is 5-[2-[(2,6-dichloro-3-methylphenyl)amino]phenyl]-1,3,4-oxadiazol-2-yl-guanidine monohydrochloride.
18. A compound of claim 1 which is 5-[2-[(2,6-dichloro-3-methylphenyl)amino]phenyl]-1,3,4-oxadiazol-2-yl-cyanamide.
19. A compound which is N-[2-[5-(methylthio)-1,3,4-oxadiazol-2-yl]phenyl]-3-trifluoromethyl benzenamine.
20. A compound which is N-[2-[5-(methylsulfonyl)-1,3,4-oxadiazol-2-yl]phenyl]-3-trifluoromethyl benzenamine.
21. A compound which is 5-[2-[[3-(trifluoromethyl)phenyl]amino]phenyl]-1,3,4-oxadiazol-2-yl-cyanamide.
22. A pharmaceutical composition for use as an antiinflammatory agent comprising an antiinflammatory amount of the compound of claim 1 and a pharmaceutical carrier.
23. A method of treating inflammation in a mammal suffering therefrom which comprises administering the compound of claim 1 in unit dosage form.
24. A compound which is 5[2-[(2,6-dichloro-3-methylphenyl)amino]phenyl]-1,3,4-oxadiazol-2(3H)-one.

25. A compound being 5[2-[(2,6-dichloro-3-methylphenyl)amino]phenyl]-1,3,4-oxadiazol-2(3H)-one.

26. A compound of claim 25 which is the sodium salt thereof.

27. A compound being 5-[2-[[3-trifluoromethyl)phenyl]amino]phenyl]-1,3,4-oxadiazol-2(3H)-thione.

28. A compound which is 5-[2-[(2,3-dimethylphenyl)amino]phenyl]-1,3,4-oxadiazol-2(3H)-one.

29. A compound being 5-[2-[(3-trifluoromethylphenyl)amino]phenyl]-1,3,4-oxadiazole-2(3H)-thione, sodium salt.

30. A compound being 5-[2-[(3-trifluoromethylphenyl)amino]phenyl]-1,3,4-oxadiazole-2(3H)-thione, choline salt.

31. A compound which is 5-[2-[[3-(trifluoromethyl)phenyl]amino]phenyl]-1,3,4-oxadiazol-2-yl-guanidine hydrochloride.

\* \* \* \* \*